United States Patent [19]

Strung

[11] Patent Number: 4,769,026
[45] Date of Patent: Sep. 6, 1988

[54] METHOD AND APPARATUS FOR PURGING A SYRINGE

[75] Inventor: Mark E. Strung, Dublin, Ohio

[73] Assignee: Erbamont, Inc., Dublin, Ohio

[21] Appl. No.: 898,156

[22] Filed: Aug. 19, 1986

[51] Int. Cl.⁴ ............................................... A61J 1/00
[52] U.S. Cl. ..................................... 604/415; 604/88; 604/263
[58] Field of Search .................... 604/86–88, 604/125, 126, 190, 197, 198, 263, 410, 411, 414, 415, 408; 55/159; 422/58, 102

[56] References Cited

U.S. PATENT DOCUMENTS

| | | | |
|---|---|---|---|
| 2,186,888 | 1/1940 | Tullar et al. | 604/415 |
| 2,812,231 | 11/1957 | Zar | 604/415 |
| 3,306,291 | 2/1967 | Burke | 604/110 |
| 3,354,881 | 11/1967 | Bloch | 604/198 |
| 3,446,596 | 5/1969 | Salivar et al. | 442/58 |
| 4,198,971 | 4/1980 | Noiles | 604/126 |
| 4,226,236 | 10/1980 | Genese | 604/125 |
| 4,312,349 | 1/1982 | Cohen | 604/415 |
| 4,534,757 | 8/1985 | Geller | 604/126 |
| 4,619,651 | 10/1986 | Kopfer et al. | 604/414 |
| 4,671,331 | 6/1987 | Pruden | 141/98 |

Primary Examiner—Dalton L. Truluck
Assistant Examiner—Frank Wilkens
Attorney, Agent, or Firm—Smith & Schnacke

[57] ABSTRACT

A syringe purging device comprises a liquid-tight chamber into which air and/or any excessive amount of a hazardous liquid, such as a chemotherapy drug, is ejected from a syringe to overcome the health hazard created by openly purging syringes into the air or into a pad of gauze material. A sharp open end of a hollow needle of a syringe is sealingly inserted into the liquid-tight chamber, and the syringe is activated to purge any air and/or excess liquid into the chamber. The liquid-tight chamber may be closed, with any liquid ejected thereinto being retained by absorption into a wad of absorbent material contained within the chamber. Alternately, the chamber may be vented to the atmosphere through a hydrophobic filter such that air injected into the chamber passes through the filter, but any liquid is retained within the chamber since it cannot pass through the hydrophobic filter. After the syringe is purged of any air and/or excess liquid, its needle is then withdrawn from the chamber or extended beyond the chamber such that the syringe may be used for an injection.

13 Claims, 2 Drawing Sheets

U.S. Patent  Sep. 6, 1988  Sheet 1 of 2  4,769,026
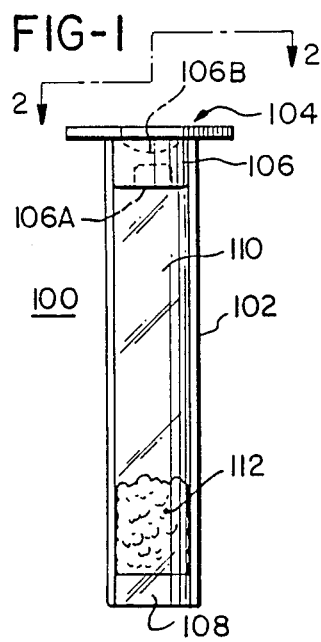
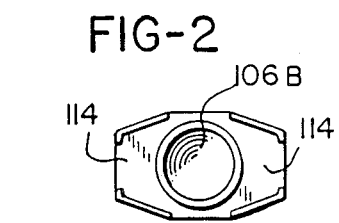
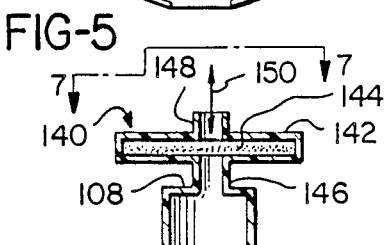
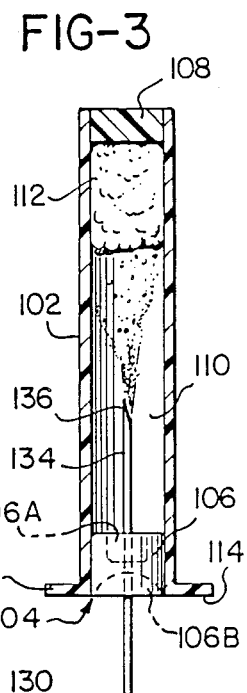
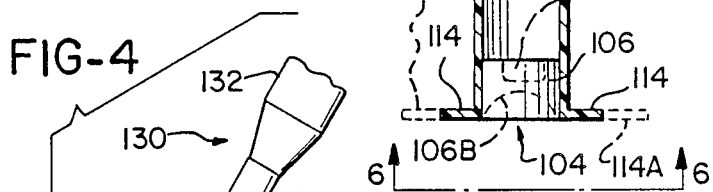
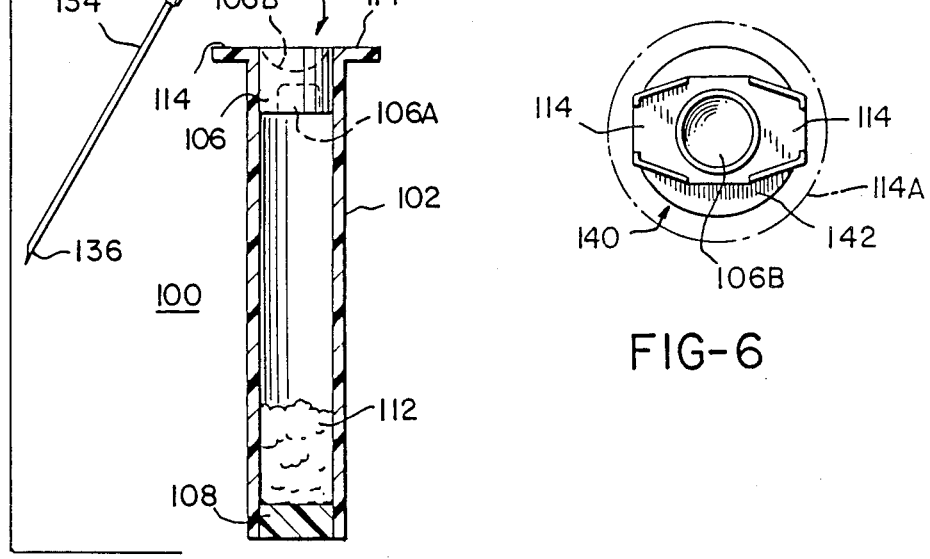
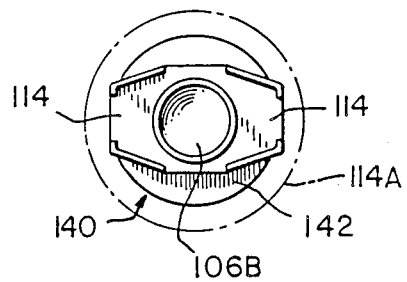

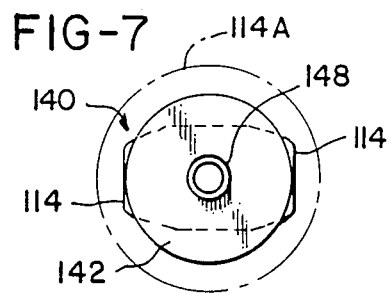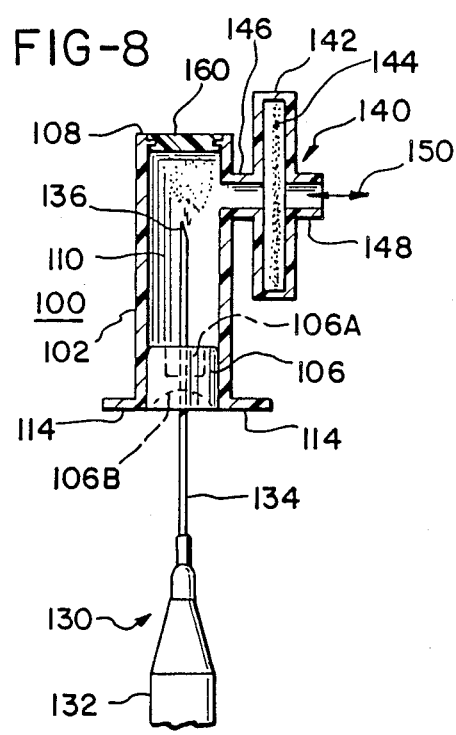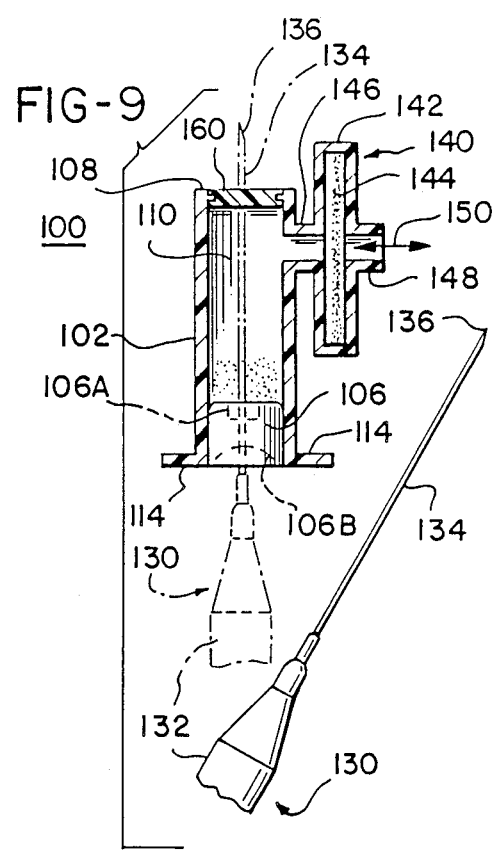

METHOD AND APPARATUS FOR PURGING A SYRINGE

BACKGROUND OF THE INVENTION

The present invention relates generally to syringes for the injection of medicines into the body, and more particularly, to a method and apparatus for catching fluids ejected from the needle of a syringe containing a hazardous or potentially hazardous liquid, such as a chemotherapy drug, as air and/or excess liquid is purged from the syringe.

The use of syringes for the hypodermic injection of medicines into the body through a hollow needle fixedly or detachedly forming a part of a syringe is commonplace in modern medicine. Preparation of a syringe for a hypodermic injection comprises drawing an approximate dosage of a medicine into a barrel of the syringe from a vial by means of a plunger sealingly fitted within the barrel of the syringe. Air is almost always included within the syringe barrel or the desired dosage exceeds that which is recommended. Accordingly, the syringe is held with the open end of its hollow needle extending generally upward and the plunger is inserted into the barrel to purge the air and/or excess medicine from the syringe prior to injection.

The purging spray from the needle is ordinarily harmless and may be simply squirted into the air or into a pad of gauze material. However, some fluids held by a syringe for injection or otherwise are hazardous or potentially hazardous, for example, chemotherapy drugs, for which the present invention is particularly applicable. When working with such fluids, the conventional purging operation described creates a dangerous health hazard to personnel utilizing the syringe. It is, thus, apparent that the need exists for a method and apparatus for purging a syringe to catch the spray which squirts from the open end of a hollow needle of a syringe when air and/or excessive portions of a hazardous or potentially hazardous liquid are ejected from the syringe to purge it.

SUMMARY OF THE INVENTION

In accordance with the present invention, the health hazard created by openly purging air and/or an excessive amount of a hazardous liquid, in particular a chemotherapy drug, from a syringe is overcome by catching the fluids purged from a syringe within a liquid-tight chamber. Liquidtight chamber as used herein means that liquid cannot enter or exit the chamber other than being injected thereinto by means of the needle of a syringe which is sealingly inserted into the chamber.

According to one aspect of the present invention, a device for purging a syringe to catch fluids ejected therefrom comprises a liquidtight chamber for receiving the sharp open end of a hollow needle of a syringe therewithin such that the syringe can be activated to purge any air and/or excess liquid from the syringe into the chamber, and containment means associated with the chamber for preventing escape from the chamber of any liquid ejected thereinto.

In a first embodiment of the syringe purging device of the present invention, the chamber comprises a closed tubular member, one end of which is closed by stopper means for maintaining an airtight seal of the tubular member and permitting sealed entrance thereinto by a needle of a syringe puncturing the stopper means. In this embodiment, the containment means comprises a wad of absorbent material enclosed within the tubular member whereby any liquid injected into the chamber is absorbed by the absorbent material. The syringe purging device may further comprise flange means extending from the one end of the tubular member which is closed by the stopper means to facilitate handling and use of the device. Preferably, the tubular member of the syringe purging device of the present invention is formed from plastic and the stopper is formed from rubber, both of which are inert to liquids to be held by the device, for example, chemotherapy drugs In a second embodiment of the syringe purging device of the present invention, the chamber comprises a tubular member closed at one end by stopper means for maintaining an airtight seal of that end of the tubular member and permitting sealed entrance thereinto by a needle of a syringe puncturing the stopper device. The other end of the tubular member is closed except for communication with containment means which comprises a hydrophobic filter such that any air injected into the chamber or needed to replace liquid withdrawn therefrom is filtered by and passes through the hydrophobic filter out of or into the tubular member, and any liquid injected into the chamber is retained therein since it cannot pass through the hydrophobic filter.

A syringe may be purged using the second embodiment by inserting the open end of the hollow needle of a syringe into the chamber through the stopper and activating the syringe to eject any air and/or excess liquid therefrom. Air ejected from the syringe is filtered by and passes through the hydrophobic filter to exit the tubular member, while any excess liquid ejected from the syringe enters the chamber and is retained therein since it cannot pass through the hydrophobic filter. The needle is then withdrawn from the stopper such that it can be used for an injection. Alternately, the closed other end of the tubular member opposite to the stopper may include diaphragm means for permitting sealed extension of a needle of a syringe beyond the chamber by puncturing the diaphragm. If the device is operated in this manner, the syringe purging device remains on the needle while it is used for injection, typically into an intravenous tube or the like, and then is discarded with the syringe. Syringe purging devices of the present invention can be conveniently included in a needle cover, for example for a prefilled syringe, to facilitate handling and use of hazardous liquids, and particularly, chemotherapy drugs.

According to another aspect of the present invention, a method for purging a syringe to catch fluids ejected from a sharp open end of a hollow needle of a syringe containing a hazardous or potentially hazardous liquid as air and/or excess liquid is purged from the syringe comprises the steps of: inserting the sharp open end of a hollow needle of a syringe into a liquidtight chamber; manually operating the syringe to purge air and/or excess liquid from the syringe; retaining any ejected liquid within the chamber; and withdrawing the needle from the chamber or extending the needle beyond the chamber. In a method for purging a syringe in accordance with the present invention, the liquidtight chamber may be closed and the step of retaining any ejected liquid within the chamber then comprises absorbing any ejected liquid in absorbent material within the chamber Alternately, the liquidtight chamber may be vented through a hydrophobic filter and then the step of retaining any ejected liquid within the chamber comprises blocking passage of liquid from the chamber through the hydrophobic filter.

It is, therefore, an object of the present invention to provide a method and apparatus for minimizing the health hazards associated with the use of a syringe containing hazardous or potentially hazardous liquids, particularly chemotherapy drugs.

Another object of the present invention is to provide an improved method and apparatus for catching fluids which squirt from the needle of a syringe containing a hazardous or potentially hazardous liquid as air and/or excessive amounts of the liquid are purged from the syringe.

An additional object of the present invention is to provide a method and apparatus for catching fluids ejected from a sharp open end of a hollow needle of a syringe containing hazardous or potentially hazardous liquids, in particular chemotherapy drugs, as air and/or excess liquid is purged from the syringe by catching the fluids purged from the syringe within a liquidtight chamber.

Other objects and advantages of the invention will be apparent from the following description, the accompanying drawings and the appended claims.

BRIEF DESCRIPTION OF THE DRAWINGS

FIG. 1 is a side view of a first embodiment of a syringe purging device in accordance with the present invention.

FIG. 2 is a top view of the syringe purging device of FIG. 1 showing the needle entryway of the device.

FIGS. 3 and 4 are partially sectioned side views of the syringe purging device of FIGS. 1 and 2 showing operation of the device for purging a syringe of air and/or excess liquid.

FIGS. 5-9 show alternate embodiments of syringe purging devices in accordance with the present invention and the usage of those embodiments.

DETAILED DESCRIPTION OF THE INVENTION

Different embodiments of a syringe purging device in accordance with the present invention are shown in the drawing figures wherein identical or corresponding parts have been identified by like reference numerals throughout. A first embodiment of a syringe purging device 100 in accordance with the present invention is shown in drawing FIGS. 1-4. The device 100 comprises a closed tubular member 102, one end 104 of which is closed by stopper means comprising a resilient stopper 106 fixedly secured within the tubular member 102. The other end 108 of the tubular member 102 preferably is formed of the same material and is contiguous with the remainder of the closed tubular member 102. The tubular member 102 thus defines a liquidtight chamber 110 which extends between the closed ends 104 and 108 of the closed tubular member 102.

While other materials can be used, preferably, the tubular member 102 is formed from translucent plastic and the stopper 108 is formed from rubber. The use of translucent plastic permits a clear view of the operation of the syringe purging device 100 to encourage proper and safe utilization. Whatever materials are used to construct a syringe purging device in accordance with the present invention, it is to be understood that they must be inert to the liquids to be used by the syringe, for example, chemotherapy drugs for which the syringe purging device is particularly useful.

The stopper 106 comprises a generally cylindrical body which includes an opening 106A positioned toward the inside of the closed tubular member 102, i.e., the chamber 110, and a concave outer wall 106B which is formed to be penetrated by the needle of a syringe with no coring action. The concave outer wall 106B is of an appropriate thickness such that it can be readily punctured by the sharp open end of a hollow needle of a syringe, and provide sealing engagement with the needle to thereby maintain the chamber 110 liquidtight yet in communication with the contents of a syringe via its hollow needle. The stopper 106 must also provide good resealability such that the fluids contained within the chamber 110 will not leak and will be retained therein for an indefinite period of time after the syringe needle is withdrawn from the stopper 106.

Fluid containment means is associated with the chamber 110 for preventing the escape of any liquid ejected into the chamber 110. In the first illustrative embodiment of the present invention shown in FIGS. 1-4, the containment means comprises a wad 112 of absorbent material, such as cotton, enclosed within the tubular member 102 such that any liquid injected into the chamber 110 is absorbed by the absorbent material. The wad 112 of absorbent material can also contain a deactivating substance to neutralize the hazardous characteristics of any liquid absorbed by the absorbent material. In the case of chemotherapy drugs, bleach is an example of one such deactivating substance.

To faciliate handling and use of the syringe purging device 100, flange means extend from the end 104 of the tubular member 102 which is closed by the stopper 106. It is noted that the flange means can be of various shapes. For example, the flange means may range from diametrically opposed planar flanges 114 shown in solid line drawings in the figures to an expanded circular flange 114A shown in dotted-line drawings in FIGS. 5-7. Expanded flanges, such as the suggested circular flange 114A, can also serve to shield and protect the user from accidental needle pricks as a syringe needle is inserted into the device 100.

Operation of the first embodiment of a syringe purging device in accordance with the present invention as shown in FIGS. 1-4 will now be described with reference particularly to FIGS. 3 and 4. A syringe 130 comprises a barrel 132 with a movable plunger (not shown) positioned therein for drawing fluids into the barrel 132 and ejecting fluids therefrom through a hollow needle 134 of the syringe 130, as is well known in the art. The sharp open end 136 of the needle 134 is inserted into a vial or dispensing container (not shown) which contains medicine to be injected by the syringe 130. The plunger is inserted entirely into the barrel 132 and then withdrawn to draw medicine from the vial into the barrel 132 for a hypodermic injection.

As is almost always the case, air will also be contained within the barrel 132 and/or the amount of medicine or other liquid desired to be drawn into the barrel 132 will exceed by a small amount the necessary quantity. In that event, the air and/or small amount of excess liquid contained within the barrel 132 must be purged prior to use of the syringe 130. As previously noted, usually the spray from the needle 134 is harmless and may be simply squirted into the air or into a pad of gauze material. However, some fluids held by the syringe 130 may be hazardous or potentially hazardous, for example, a chemotherapy drug, such that performing the purging operation in the open air or into a pad of gauze material may be hazardous to personnel utilizing the syringe. In such cases, the syringe purging device 100 of the present invention is conveniently utilized as follows.

The sharp open end 136 of the needle 134 is inserted into the chamber 110 by engaging the concave outer wall 106B of the stopper 106 preferably near its center where it is forced to puncture the stopper 106 for sealed insertion into the chamber 110 as shown in FIG. 3. The syringe 130 is then activated by forcing its plunger into the barrel 132, with the needle 134 being in a generally upward direction such that air within the barrel 132 is adjacent to and will be ejected through the needle 134 into the chamber 110 to purge the air from the barrel 132. This purging operation is shown in FIG. 3 wherein the air is injected into the chamber 110. Some portion of the liquid contained within the barrel 132 is also ejected into the chamber 110 either inadvertently with the air or to eliminate excess liquid from the barrel 132 such that a desired quantity of the liquid is contained within the barrel 132. It is noted that syringe purging devices of the present invention are sterilized such that any liquid ejected from the syringe can be redrawn into the syringe if an excessive amount of the liquid is inadvertently ejected into the chamber 110.

Once the air and/or any excess liquid has been purged from the barrel 132, the syringe 130 and syringe purging device 100 are inverted to the position shown in FIGS. 1 and 4 such that the needle is in a generally downward direction, and any liquid ejected into the chamber 110 with insufficient force to engage the wad 112 of absorbent material enclosed within the end of the chamber 110 will flow toward that end of the chamber where it too is absorbed. The syringe needle 134 can then be withdrawn from the stopper 106 such that it is ready for use as shown in FIG. 4. The absorption of any liquid ejected into the chamber 110 by the absorbent material and the resealability characteristics of the stopper 106 ensure that any liquid ejected from the syringe 130 remains within the chamber 110 as the needle 134 is withdrawn from the stopper 106.

Alternate embodiments of a syringe purging device in accordance with the present invention and the operation of those embodiments is shown in FIGS. 5-9. FIGS. 5-7 show a partially sectioned side view, bottom view and top view, respectively, of a syringe purging device 100 which comprises a tubular member 102 closed at one end 104 by stopper means comprising a resilient stopper 106 fixedly secured in the one end 104 for maintaining an airtight seal of that end of the tubular member 102. The stopper 106 permits sealed entrance into a chamber 110 defined by the tubular member 102 by a needle of a syringe puncturing the stopper 106.

The other end 108 of the tubular member 102 is closed except for communication with containment means which, in this embodiment of the syringe purging device 100, comprises a hydrophobic filter 140. While the hydrophobic filter may take any of a number of forms, in the illustrated embodiment, it comprises a circular disc-like housing 142 for holding a hydrophobic filter element 144 therewithin such that air entering the housing 142 through passages 146 and 148 must pass through the hydrophobic filter element 144. The passage 146 provides communication between the chamber 110 defined by the tubular member 102 and the hydrophobic filter 140. Air may pass through the hydrophobic filter 140 through the passages 146 and 148 as indicated by the arrow 150 such that air injected into the chamber 110 or needed to replace liquid withdrawn therefrom (for example, if excess liquid is inadvertently injected into the chamber 110) is filtered by and passes through the hydrophobic filter 140, while any liquid injected into the chamber 110 is retained therein since it cannot pass through the hydrophobic filter 140.

A syringe may be purged using the embodiment shown in FIGS. 5-7 by inserting the open end of a hollow needle of a syringe into the chamber 110 through the stopper 106 and activating the syringe to eject any air and/or excess liquid therefrom. Air ejected from the syringe is filtered by and passes through the hydrophobic filter 140 to exit the tubular member 102, while any excess liquid ejected from the syringe enters the chamber and is retained therein since it cannot pass through the hydrophobic filter 140. The needle is then withdrawn from the stopper 106 such that it can be used for an injection.

An alternate of the embodiment of the syringe purging device 100 of FIGS. 5-7 is shown in FIGS. 8 and 9. In this embodiment, the liquidtight chamber 110 is vented through a hydrophobic filter 140 which is placed in communication with the chamber 110 on the side of the tubular member 102. The closed other end of the tubular member 102 opposite to the stopper 106 may then include diaphragm means 160 for permitting sealed extension of a needle of a syringe beyond the chamber 110 by puncturing the diaphragm 160. If the device 100 of FIGS. 8 and 9 is used in this manner, the device 100 remains on the needle as it is used for injection, typically into an intravenous tube or the like, and then the device 100 is discarded with the syringe.

A syringe may be purged using this embodiment by inserting the sharp open end 136 of the hollow needle 134 of the syringe 130 into the chamber 110 through the stopper 106 and activating the syringe to eject any air and/or excess liquid therefrom. Air ejected from the syringe 130 is filtered by and passes through the hydrophobic filter 140 to exit the tubular member 102, while any excess liquid ejected from the syringe 130 enters the chamber 110 and is retained therein since it cannot pass through the hydrophobic filter 140. The needle may then be withdrawn from the stopper as shown by the solid line drawing in FIG. 9 such that it can be used for an injection. Alternately, the sharp open end 136 of the needle 134 can be extended beyond the chamber 110 by puncturing the diaphragm 160 as shown by the dotted line drawing in FIG. 9.

It is noted that the stoppers 10 syringe purging devices in accordance with the present invention could be diaphragms or the like which would close the devices as described, yet permit sealed penetration of a syringe needle therethrough. The syringe purging devices of the present invention can also be conveniently included in a needle cover. If such a needle cover is used on a prefilled syringe, the syringe can be purged and ready for administration of an injection before the cover is removed. In syringes which are not prefilled, the syringe needle can be reinserted into the previously removed needle cover to perform the purging operation.

While the methods herein described and the forms of apparatus for carrying these methods into effect constitute preferred embodiments of this invention, it is to be understood that the invention is not limited to these precise methods and forms of apparatus, and that changes may be made in either without departing from the scope of the invention which is defined in the appended claims.

What is claimed is:

1. A device for retaining and neutralizing hazardous fluids ejected from an open end of a hollow needle of a syringe, comprising:

a member havign a sealed interior chamber and a portion, communicating with said chamber, adapted to be pierced by said needle end such that said needle end enters said chamber; and means within said chamber for retaining said hazardous fluid thereon, said retaining means including means for neutralizing hazardous characteristics of said hazardous fluid;

whereby said syringe may be safely purged by inserting said needle end thereof said portion and purging said hazardous fluid therefrom into said chamber, such that said fluid is retained and neutralized by said retaining means.

2. The device of claim 1 further comprising flange means extending from said member adjacent to said portion to facilitate handling and use of said device.

3. The device of claim 1 wherein said portion includes stopper means for permitting sealed entrance into said chamber by said needle end.

4. The device of claim 1 wherein saisd member includes diaphragm means, communicating with said chamber and positioned on said member opposite said portion, for permitting sealed extension of said needle simultaneously through said portion, said chamber and said diaphragm means.

5. The device of claim 1 wherein said retaining means comprises a wad of absorbent material.

6. The device of claim 5 wherein said material comprises cotton.

7. The device of claim 1 further comprising means forming a hydrophobic filter between said chamber and the atmosphere.

8. A device for catching fluids ejected from a sharp open end of a hollow needle of a syringe containing a hazardous liquid as air and excess liquid are purged from the syringe, comprising:

a liquidtight cahmber, for receiving said needle end therein, including a closed tubular member, stopper means closing an end of said tubular member for maintaining an airtight seal of said tubular member and permitting sealed entrance therein by said needle;

containment means associated with said chamber for preventing escape from said chamber of liquid ejected from said needle, said containment means including a wad of absorbent material containing a deactivating substance for neutralizing hazardous characteristics of liuquid ejected into said chamber; and flange means extending from said end of said tubular member to facilitate handling and use of said device;

whereby said syringe may be purged by inserting said needle thereof into said chamber and activating said syringe to eject air and/or excess liquid therefrom such that aid excess liquid is retained within said chamber as said needle is withdrawn from or extened beyond said chamber.

9. The syringe purging device of claim 8 wherein said tubular member is formed from plastic and said stopper means is formed from rubber.

10. A device for catching fluids ejected from a sharp open end of a hollow needle of a syringe containing a hazardous liquid as air and excess liquid are purged from the syringe, comprising:

a liquidtight chamber, for receiving said needle end therein, including a closed tubular member, stopper means closing an end of said tubular member for maintaining an airtight seal of said tubular member and permitting sealed entrance therein by said needle; and containment means associated with saids chamber for preventing escape from said chamber of liquid ejected from said needle, said contaiment means including a wad of absorbent material containing a deactivating substance for neutralizing hazardous characteristics of liquid ejected into said chamber;

whereby said syringe may be purged by inserting said needle thereof into said chamber and activating said syringe to eject air and/or excess liquid therefrom such that saids excess liquid is retained within said chamber as said needle is withdrawn from or extended beyond said chamber.

11. A method for catching fluids ejected from a sharp open end of a hollow needle of a syringe containing a hazardous liquid as air and/or excess liquid is purged from the syringe, comprising the steps of:

inserting said needle end into a liquidtight chamber;

purging air and excess liquid from said syringe through said needle thereof into said chamber; and retaining said purged liquid within said chamber and absorbing said liquid in absorbent material within aid chamber, said absorbent material having a deactivating substance whereby hazardous characteristics of said purged liquid absorbed by said material are neutralized.

12. The method of claim 11 further comprising the step of, subsequent to said purging step, extending said needle beyond said chamber.

13. The method of claim 11 further comprising the step of venting said chamber through a hydrophobic filter to the atmosphere.

* * * * *

UNITED STATES PATENT AND TRADEMARK OFFICE
CERTIFICATE OF CORRECTION

PATENT NO. : 4,769,026
DATED : September 6, 1988
INVENTOR(S) : Mark E. Strung

It is certified that error appears in the above-identified patent and that said Letters Patent is hereby corrected as shown below:

Column 7, line 5, "havign" should be --having--.
Column 7, line 14, after "thereof" insert --through--.
Column 7, line 24, "saisd" should be --said--.
Column 7, line 42, "cahmber" should be --chamber--.
Column 8, line 7, "aid" should be --said--.
Column 8, line 9, "extened" should be --extended--.
Column 8, line 23, "saids" should be --said--.
Column 8, line 25, "contaiment" should be --containment--.
Column 8, line 32, "saids" should be --said--.
Column 8, line 44, "aid" should be --said--.

Signed and Sealed this

Fifteenth Day of August, 1989

*Attest:*

DONALD J. QUIGG

*Attesting Officer*  Commissioner of Patents and Trademarks